US00PP36713P2

(12) United States Plant Patent
Olesen

(10) Patent No.: US PP36,713 P2
(45) Date of Patent: Jun. 3, 2025

(54) ROSE PLANT NAMED 'Poulvic003'

(50) Latin Name: *Rosa hybrida*
Varietal Denomination: Poulvic003

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 18/831,182

(22) Filed: Sep. 5, 2024

(30) Foreign Application Priority Data

Sep. 22, 2023 (QZ) ..... PBR 20231985

(51) Int. Cl.
*A01H 5/02* (2018.01)
*A01H 6/74* (2018.01)

(52) U.S. Cl.
USPC ..... Plt./126

(58) Field of Classification Search
USPC ..... Plt./101.123, 126
See application file for complete search history.

*Primary Examiner* — Susan McCormick Ewoldt

(57) ABSTRACT

A new garden rose plant of the Miniature class which has abundant, yellow orange blend flowers and attractive foliage. This new and distinct variety has shown to be uniform and stable in the resulting generations from asexual propagation.

1 Drawing Sheet

Botanical designation: *Rosa hybrida.*
Variety denomination: 'Poulvic003'.

This application claims priority to Plant Breeder's Rights Application Number 2023/1985, which was filed at the Community Plant Variety Rights Office in the European Union on Sep. 22, 2023, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2014 and the resulting seeds were planted in a controlled environment in Fredensborg, Denmark. The new variety, named 'Poulvic003', originated as a single seedling from the stated cross.

The new variety may be distinguished from its male pollen parent and female seed parent primarily by the following characteristics. The male pollen parent plant has flowers which are nearly the same coloration as 'Poulvic003' however are more predominantly in orange tones. The female seed parent plant has yellow flowers while the new variety has yellow orange blend flowers.

The objective of the hybridization of this rose variety was to create a new and distinct variety with unique qualities, such as:

1. Uniform and abundant yellow orange blend flowers;
2. Vigorous, but compact growth when propagated on its own roots;
3. Exceptional disease resistance.

This combination of qualities is not present in previously available commercial cultivars of this type, known to the inventor, and distinguish 'Poulvic003' from all other varieties of which we are aware.

As part of the rose development program, Mogens N. Olesen germinated the seeds from the aforementioned hybridization during winter of 2014 and conducted evaluations on the resulting seedlings in a controlled environment in Fredensborg, Denmark. 'Poulvic003' was selected in the spring of 2015 by the inventor as a single plant from the progeny of the aforementioned hybridization.

Asexual reproduction of 'Poulvic003' by rooted cuttings was first done by Mogens N. Olesen in the nursery in Fredensborg, Denmark in July 2015. This initial and other subsequent asexual propagations conducted in controlled environments have demonstrated that the characteristics of 'Poulvic003' are true to type and are transmitted from one generation to the next.

DESCRIPTION OF THE DRAWING

The accompanying color illustration shows as true as is reasonably possible to obtain in color photographs of this type, the typical characteristics of the buds, flowers, leaves, and stems, of 'Poulvic003'.

Specifically illustrated in the drawing are open flowers viewed from the side and above, petals detached, flower bud, sepals detached revealing the receptacle, and mature leaves. Plants shown are 5 months old.

DETAILED DESCRIPTION OF THE VARIETY

The following is a description of 'Poulvic003', as observed in its growth in a glass house located in Odense Denmark. Observed plants are 5 months of age, and were grown on their own roots in 24 cm containers. Color references are made using The Royal Horticultural Society (London, England) Colour Chart, 2001, except where common terms of color are used.

For a comparison, several physical characteristics of the rose variety 'Poulpah091', U.S. Plant Pat. No. 30,350 are compared to 'Poulvic003' in Chart 1.

CHART 1

| | 'Poulvic003' | 'Poulpah091' |
|---|---|---|
| Petal Count | 35 | 55 |
| Flower Diameter | 70 mm | 80 mm |
| General Tonality of Flower Color | Open flowers are Orange Group 24C. After flowers have fully matured tonality becomes Yellow-Orange Group 16C | Yellow-Orange Group 19B with intonations of Orange Group 24C |

FLOWER AND FLOWER BUD

Blooming habit: Continuous.

Flower bud:

*Size*.—Upon opening, 25 mm in length from base of receptacle to end of bud. Bud diameter is 15 mm.

*Bud form*.—Ovoid.

*Bud color*.—As sepals divide petals are Orange Group 26B and Yellow Group 8B.

*Sepal inner surface*.—Color: Yellow-Green Group 146D. Surface: Lightly pubescent.

*Sepal outer surface*.—Color: Yellow-Green Group 144A. Texture: Smooth.

*Sepal shape*.—Apex: Cirrhose. Base: Flat at union with receptacle.

*Sepal margin*.—Margins have weak foliaceous appendages on three of the five sepals.

*Sepal size*.—About 25 mm long, 7 mm wide.

*Receptacle*.—Texture: Smooth. Size: 7 mm in height, 9 mm wide. Color: Yellow-Green Group 144A. Shape: Campanulate.

*Pedicel*.—Surface: Smooth. Length: 52 mm average. Diameter: 2 mm. Color: Yellow-Green Group 144A. Strength: Strong.

Flower bud development: Flower buds are borne singular or in clusters of about 5 flower buds pe stem.

Flower bloom:

*Fragrance*.—Moderate floral scent.

*Duration*.—The blooms have a duration on the plant of approximately 20 days. Petals fall cleanly away from plant after flowers have fully matured.

*Size*.—Flower diameter is 70 mm when open. Flower depth is 31 mm.

*Flower shape*.—High centered, double, with a high pointed center which is tightly closed.

*Shape of flower, side view*.—The upper and lower portions are flat.

Petalage: Under normal conditions, flowers have about 35 petals.

General tonality of flower: Open flowers are Orange Group 24C. After flowers have fully matured tonality becomes Yellow-Orange Group 16C.

Petal color:

*Upon opening, outer petals*.—Upper surface: Yellow-Orange Group 22B splashed with Yellow Group 9B. At the basal zone Yellow Group 9A. Lower surface: Yellow Group 8B shaded with strong intonations of Orange Group 24B.

*Upon opening, inner petals*.—Upper surface: Basal zone Yellow Group 9A. Yellow Group 22B at middle and marginal zone. Lower surface: Basal zone Yellow Group 9A. Middle and marginal zone Yellow-Orange Group 19A. Other intonations Yellow Group 12C.

*After opening, outer petals*.—Upper surface: Orange-Red Group 27B at middle and marginal zone. Basal zone Yellow Group 4B. Lower surface: Basal zone Yellow Group 4B. Middle and marginal zone Orange Group 27B.

*After opening, inner petals*.—Upper surface: Yellow Group 12C with shades of Yellow-Orange Group 16B. Lower surface: Yellow Group 12C with shades of Yellow-Orange Group 16B.

Petals:

*Petal reflex*.—Strong, bilateral.

*Margin*.—Entire and uniform. No undulations on outer petals. Inner petals have strong undulations.

*Shape*.—Broad and elliptic. Apex shape: Rounded. Base shape: Acute.

*Size*.—35 mm (l)×36 mm (w).

*Texture*.—Smooth.

*Thickness*.—Average.

Petaloids:

*Size*.—25 mm (l) by 13 mm (w).

*Quantity*.—About 5.

*Shape*.—Irregular with undulated margins. The base is acute and the apex is round.

*Color*.—The upper surface is Yellow Group 12C with shades of Yellow-Orange Group 16B. The lower surface is Yellow Group 12C with shades of Yellow-Orange Group 16B.

Reproductive flower parts:

*Pollen*.—None observed.

*Anthers*.—Size: 3 mm in length. Color: Yellow Group 12D. Quantity: 55 on average.

*Filaments*.—Color: Yellow Group 14A. Length: 8 mm.

*Pistils*.—Length: 6 mm. Quantity: 32 on average.

*Stigmas*.—Color: Greyed-Yellow Group 162D.

*Styles*.—Color: Red-Purple Group 61C.

*Location of stigmas*.—Inferior in location relative to the length of the filaments and the height of the anthers.

*Hips*.—None Observed.

PLANT

Plant growth: Upright. Plants are about 63 cm in height, and 40 cm wide.

Stems:

*Color of juvenile growth*.—Yellow-Green Group 144B.

*Color of mature growth*.—Yellow-Green Group 144A.

*Length*.—Canes are about 38 cm from the base of the plant to the flowering portion.

*Diameter*.—About 4 mm.

*Internodes*.—On mature canes about 35 mm between nodes.

*Surface texture*.—Young wood: Smooth. Older wood: Smooth.

Long prickles: None observed.

Plant foliage:

*Compound leaf*.—115 mm (l)×80 (w).

*Quantity*.—About 3 leaves per 10 cm of stem on average.

*Leaf bearing angle to the stem*.—45 degrees.

*Color of juvenile foliage*.—Upper side: Yellow-Green Group 147A. Petioles have Greyed-Purple Group 183A coloration. Lower side: Yellow-Green Group 147B.

*Color of mature foliage*.—Upper side: Yellow-Green Group 147A. Lower side: Yellow-Green Group 147B.

Plant leaves and leaflets:

*Stipules*.—Size: 13 mm long, 5 mm wide. Quantity: 2 per compound leaf. Shape: Linear, slightly broad based with. outward extending apices. Margins: Finely serrated. Color.

*Petiole*.—Length: 10 mm. Diameter: 1.5 mm. Upper surface color: Yellow-Green Group 144A. Lower surface color: Yellow-Green Group 144A.

*Rachis*.—Length: About 52 mm. Upper surface color: Yellow-Green Group 144A. Lower surface color: Yellow-Green Group 144A.

*Leaflet*.—Quantity: Normally 5 to 7 leaflets. Margins: Serrated. Size: Terminal leaflets are about 48 mm long, 38 mm wide. Shape: Generally elliptical. Base: Rounded. Apex: Acute. Texture: Smooth. Thickness: Average. Arrangement: Odd pinnate. Venation: Reticulate. Glossiness: Not glossy.

*Disease resistance*.—Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

*Cold hardiness*.—The variety is tolerant to USDA Cold Hardiness Zone 6.

*Heat tolerance*.—The variety has been found to be suitable for climate conditions found in the American Horticulture Society heat zone 7.

I claim:

1. A new and distinct variety of rose plant named 'Poulvic003' substantially as described and illustrated herein.

* * * * *

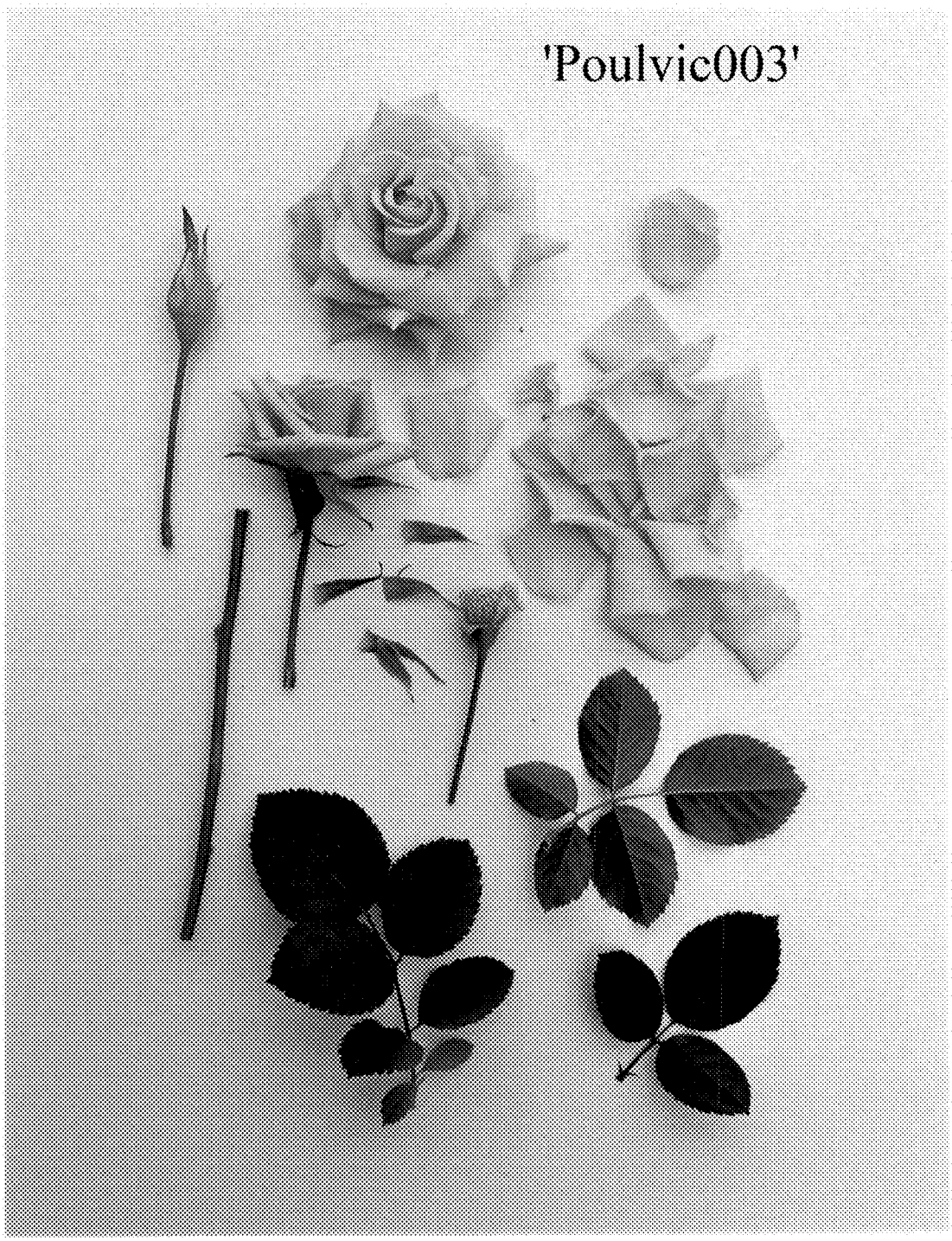
'Poulvic003'